United States Patent
Wegerer et al.

(10) Patent No.: US 9,238,600 B2
(45) Date of Patent: Jan. 19, 2016

(54) DUAL RISER CATALYTIC CRACKER FOR INCREASED LIGHT OLEFIN YIELD

(75) Inventors: David A. Wegerer, Des Plaines, IL (US); Brian W. Hedrick, Des Plaines, IL (US); Zhihao Fei, Des Plaines, IL (US); Daniel N. Myers, Des Plaines, IL (US); Vincenza Myers, legal representative, Arlington Heights, IL (US); Paolo Palmas, Des Plaines, IL (US); Laura E. Leonard, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 450 days.

(21) Appl. No.: 13/325,292

(22) Filed: Dec. 14, 2011

(65) Prior Publication Data

US 2013/0158326 A1    Jun. 20, 2013

(51) Int. Cl.
| | |
|---|---|
| *C07C 4/06* | (2006.01) |
| *C10G 51/02* | (2006.01) |
| *C10G 11/05* | (2006.01) |
| *C10G 11/18* | (2006.01) |

(52) U.S. Cl.
CPC . *C07C 4/06* (2013.01); *C10G 11/05* (2013.01); *C10G 11/18* (2013.01); *C10G 51/026* (2013.01); *C07C 2521/04* (2013.01); *C07C 2521/08* (2013.01); *C07C 2521/16* (2013.01); *C07C 2529/40* (2013.01); *C07C 2529/50* (2013.01); *C07C 2529/65* (2013.01); *C10G 2400/20* (2013.01)

(58) Field of Classification Search
CPC .................................. C07C 4/06; B01J 19/00
See application file for complete search history.

(56) References Cited

U.S. PATENT DOCUMENTS

| | | | | |
|---|---|---|---|---|
| 4,914,255 A | * | 4/1990 | Avidan et al. | 585/661 |
| 5,002,915 A | * | 3/1991 | Harandi et al. | 502/51 |

(Continued)

FOREIGN PATENT DOCUMENTS

| | | |
|---|---|---|
| CN | 101293806 A | 10/2008 |
| EA | 009221 B1 | 12/2007 |

OTHER PUBLICATIONS

Hemler C L; Upson L L, Maximising FCC propylene production, European Refining Technology Conference (Berlin Nov. 16-18, 1998) (Adaptation) Petroleum Technology Quarterly (ISSN 1362-363) V4 N.2 31,33-35 (Summer 1999), Jun. 1999.

(Continued)

*Primary Examiner* — In Suk Bullock
*Assistant Examiner* — Sharon Pregler
(74) *Attorney, Agent, or Firm* — James C. Paschall

(57) ABSTRACT

A process for improving the yield of ethylene and propylene from a light naphtha feedstock includes obtaining light naphtha feedstock from a primary cracking zone having a cracking catalyst. The light naphtha feedstock is contacted with an olefin catalyst in an olefin producing zone to produce an ethylene- and propylene-rich stream. After reacting with the olefin catalyst, the ethylene- and propylene-rich stream is separated from the olefin catalyst from in a separator zone. At least a portion of the olefin catalyst is regenerated by combusting coke deposited on a surface of the olefin catalyst in an oxygen-containing environment, and at least a portion of the olefin catalyst is heated. These portions could be the same one or they could be different. In some embodiments, at least a portion of the olefin catalyst could be neither regenerated nor heated. The olefin catalyst is returned to the olefin producing zone.

16 Claims, 5 Drawing Sheets

(56) References Cited

U.S. PATENT DOCUMENTS

| | | | |
|---|---|---|---|
| 6,049,017 A * | 4/2000 | Vora et al. | 585/324 |
| 6,106,697 A | 8/2000 | Swan | |
| 7,041,259 B2 * | 5/2006 | Cammy et al. | 422/145 |
| 7,259,287 B2 | 8/2007 | Beech et al. | |
| 7,323,099 B2 * | 1/2008 | Henry | 208/67 |
| 2001/0052482 A1 | 12/2001 | Winter | |
| 2006/0108260 A1 | 5/2006 | Henry | |
| 2008/0035527 A1 | 2/2008 | Eng et al. | |
| 2009/0288985 A1 | 11/2009 | Long et al. | |
| 2010/0022810 A1 | 1/2010 | Sekiguchi et al. | |
| 2010/0324232 A1 | 12/2010 | Mo et al. | |
| 2011/0000818 A1 | 1/2011 | Xu et al. | |
| 2011/0108458 A1 | 5/2011 | Leonard et al. | |

OTHER PUBLICATIONS

Li, Xiaohong; Chen, Xiaobo; Li, Chunyi; Zhang, Jianfang; Yang, Chaohe; Shan, Honghong, Two-stage riser fluidized-bed catalytic cracking technology for production of propylene, Shiyou Huagong/Petrochemical Technology, v 35, n 8, p. 749-753, Aug. 2006.

Li, Chun-Yi; Yuan, Qi-Min; Chen, Xiao-Bo; Yang, Chao-He; Shan, Hong-Hong; Zhang, Jian Fang, Maximizing yield of propylene by two-stage riser catalytic pyrolysis of heavy oil, Zhongguo Shiyou Daxue Xuebao (Ziran Kexue Ban)/Journal of China University of Petroleum (Edition of Natural Science), v 31, n 1, p. 118-121, Feb. 2007.

Yan, Shaochun; Wang, Longyang; Meng, Fandong; Zhang, Lixin; Qiao, Ligong, FDFCC-III process for propylene production, Energy Institute—19th World Petroleum Congress 2008: A World in Transition: Delivering Energy for Sustainable Growth, v 2, p. 942, 2008.

Search Report dated Dec. 20, 2012 for corresponding PCT Appl. No. PCT/US2012/057715.

* cited by examiner

DUAL RISER CATALYTIC CRACKER FOR INCREASED LIGHT OLEFIN YIELD

FIELD OF THE INVENTION

This invention relates to increasing yields of ethylene and propylene in refinery processes. More specifically, it relates to a process for increasing yields of ethylene and propylene in an energy efficient manner.

BACKGROUND OF THE INVENTION

In typical refinery operations, vacuum gas oil produced in a vacuum distillation column is fed to a catalytic cracking zone to produce naphtha and distillate fuels which are higher in value. When operating toward this goal, the catalytic cracking zone is operated under a given set of conditions to increase the yield of these desired products. During the cracking reactions, carbon, in the form of coke, deposits on the surface of the catalyst. The coke is burned from the catalyst in a regeneration zone in the presence of oxygen to promote combustion. Because the amount of coke is so great and combustion so intense, catalyst coolers are sometimes used to reduce the catalyst temperature prior to being reintroduced into the catalytic cracking zone.

However, when the goal is to produce light olefins, such as ethylene and propylene, catalysts and process conditions conducive to the catalytic cracking processes used to reduce the average molecular weight of gas oil or residual oils ("resids") are not optimum for converting the naphtha from a catalytic cracking zone to light olefins, such as ethylene and propylene. There is a benefit to separating the catalytic cracking zone from an olefin producing zone.

When the reaction zones and the regeneration zones for the catalytic cracking and olefin production zones were separated, it was found that less coke is deposited on the surface of the olefin producing catalyst because of the nature of the feedstock to the process. Light hydrocarbons, such as naphtha or light naphtha, produce significantly less coke than cracking of resids or gas oils. Combustion of the coke may not be sufficient to supply enough heat to an olefin producing zone for efficient olefin production. It was found that there was a need in the art for a way to separate the catalytic cracking and olefin producing functions, while maintaining a suitable yield of light olefins. There was a further need in the art for a process or reactor system that generates light olefins in a more energy efficient manner.

SUMMARY OF THE INVENTION

These and other needs are at least partially addressed by the invention described herein. A process for improving the yield of ethylene and propylene from a light naphtha feedstock includes obtaining light naphtha feedstock from a primary cracking zone having a cracking catalyst. The light naphtha feedstock is contacted with an olefin catalyst in an olefin producing zone to produce an ethylene- and propylene-rich stream. After reacting with the olefin catalyst, the ethylene- and propylene-rich stream is separated from the olefin catalyst in a separator zone. At least a portion of the olefin catalyst is regenerated by combusting coke deposited on a surface of the olefin catalyst in an oxygen-containing environment, and at least a portion of the olefin catalyst is heated. These portions could be the same one or they could be different. In some embodiments, at least a portion of the olefin catalyst could be neither regenerated nor heated. The olefin catalyst is returned to the olefin producing zone.

Separation of the primary cracking zone and an olefin producing zone allows each of these processes to be optimized. Different catalysts can be used in each reaction zone. Process conditions are selected in the cracking zone and the olefin producing zone that increase the yield of desirable products such as ethylene and propylene.

Heating of the catalyst further improves the yield of desirable light olefins, such as ethylene and propylene. Providing additional heat to the olefin catalyst allows suitable yields of light olefins despite the low coke deposition on the olefin catalyst in comparison to coke generated in a conventional catalytic cracking zone by processing of gas oils or resid. Even when regeneration of the olefin catalyst does not generate sufficient heat to bring the olefin producing catalyst to the optimum temperature for the optimum olefin production, improved yields can be accomplished by externally supplying heat. Increasing heat to the olefin producing zone increases the reaction temperature and improves the yield of the desired light olefins. Further, when the olefin is heated using a heat source of excess or waste heat, the energy efficiency of the refinery is improved.

DETAILED DESCRIPTION OF THE DRAWINGS

DETAILED DESCRIPTION OF THE INVENTION

Figure 1:
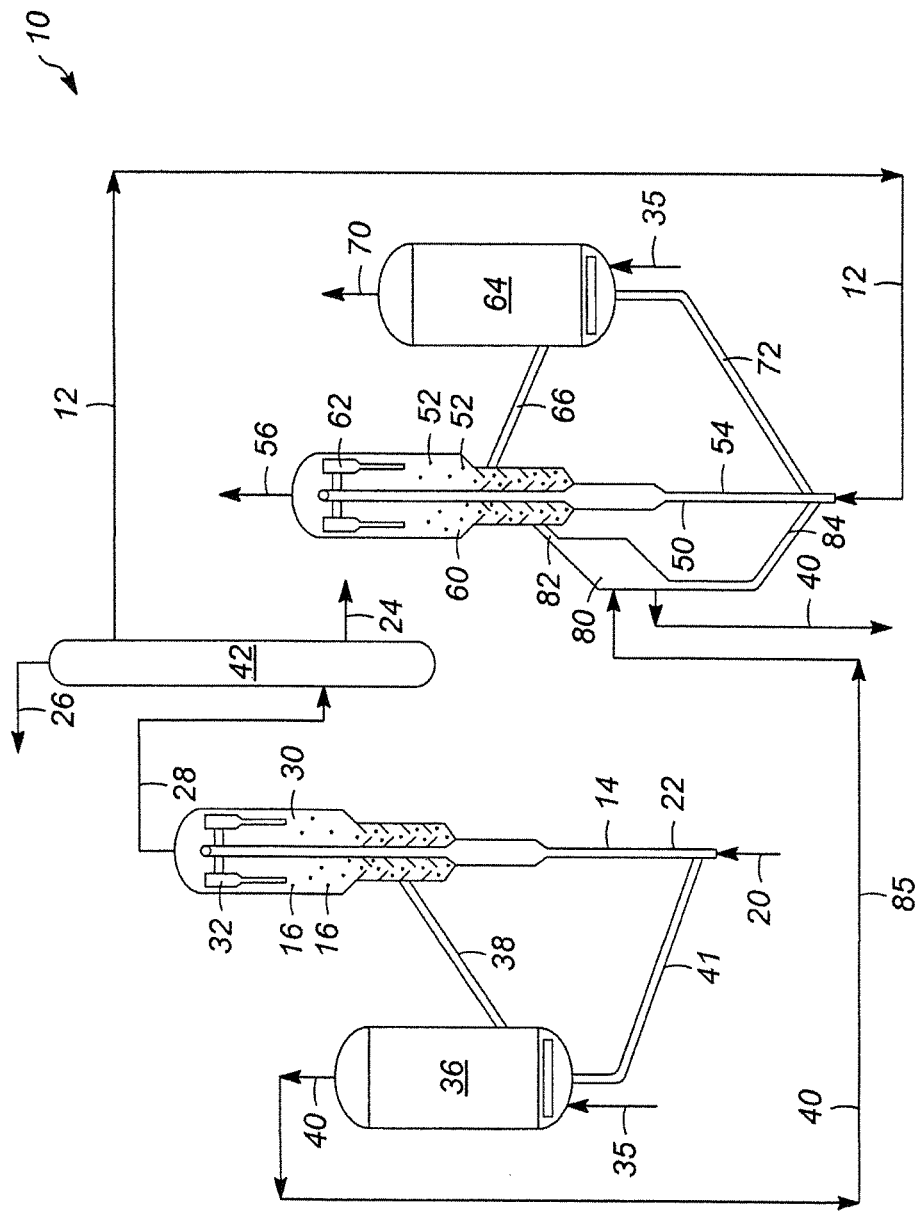
FIG. 1 is a schematic drawing of a first embodiment of the invention.

Referring to FIG. 1, light naphtha feedstock 12 is obtained from a primary catalytic cracking zone 14 utilizing a cracking catalyst 16 for a process, generally 10, for increasing ethylene and propylene yield. Any catalytic cracking process or apparatus may be used as the primary cracking zone 14, including those adapted to process catalytic cracking feedstocks 20 that include, but are not limited to atmospheric or vacuum residual oils, atmospheric or vacuum gas oils or feedstocks for producing olefins for petrochemicals. Examples of these processes include a fluidized catalytic cracking ("FCC") process, a residual oil FCC ("RFCC") process or the PetroFCC® process, a cracking process designed to optimize olefin production, all licensed by UOP, LLC.

In some exemplary embodiments, the catalytic cracking zone 14 uses a fluidized process. The cracking catalyst 16 is combined with a lift gas and a catalytic cracker feedstock 20 at the entrance to a first riser reactor 22. As these components travel the length of the riser reactor, the catalytic cracker feedstock 20 reacts in the presence of the cracking catalyst 16 to generate products 28 lower in molecular weight than the catalytic cracking feedstock 20. Typical products 28 include light cycle oils 24, light naphtha 12, and a light ends stream 26. For the purposes of this invention, light naphtha 12 is considered to be for example, $C_4$ to $C_{10}$ naphtha, preferably $C_4$ to $C_7$ light naphtha with an olefin content of at least about 5 wt % and preferably at least about 10 to about 30 wt %.

In the catalytic cracking zone 14, the catalytic cracker feedstock 20 is contacted with a cracking catalyst 16 that promotes cracking of heavy oils to lighter, more valuable, products. Catalysts that promote cracking include, but are not limited to large pore molecular sieves. Typically, molecular sieves with a large pore size have pores with openings of greater than 0.7 nm in effective diameter defined by greater than 10 and typically 12 membered rings. Pore Size Indices of large pores are above about 31. Suitable large pore zeolite components include synthetic zeolites such as X-type and Y-type zeolites, mordenite and faujasite. It has been found that Y zeolites with low rare earth content are preferred as the cracking catalyst component. Low rare earth content denotes less than or equal to about 1.0 wt % rare earth oxide on the zeolite portion of the catalyst. Octacat™ catalyst made by W. R. Grace & Co. is an example of a suitable low rare earth Y-zeolite catalyst.

The cracking zone is operated at any useful process conditions. Temperatures range from 510° C. (950° F.) to about 593° C. (1100° F.). Pressures vary between 24.7 psi (170.3 KPa) and 64.7 psi (446 KPa). The catalyst to oil ratio is from about 1 to about 30, preferably about 1 to about 20. Variations in these conditions are due to differences in feedstock, catalyst and process equipment. Residence time for the catalytic cracker feedstock 20 in contact with the cracking catalyst 16 in the riser 22 is from about 0.1 to 5 seconds, preferably less than or equal to 2 seconds. The exact residence time depends upon the catalytic cracker feedstock 20 quality, the specific catalyst 16 and the desired product 28 distribution. Short residence time assures that the desired products do not convert to undesirable products. Hence, the diameter and height of the riser 22 may be varied to obtain the desired residence time.

At the top of the catalytic cracking zone 14, the cracking catalyst 16 is dislodged from the catalytic cracker feedstock 20 and the lift gas in a first separator zone 30. In a fluidized system, some of the cracking catalyst 16 falls by gravity in an area of reduced pressure. One or more cyclones 32 can optionally be used to improve separation of the cracking catalyst 16 from the catalytic cracking products 28.

As the primary catalytic cracking feedstock 20 reacts with the cracking catalyst 16, coke deposits on the cracking catalyst 16, causing a reduction in catalyst activity. The catalyst activity is restored by burning the cracking catalyst 16 in the presence of oxygen from an oxygen source 35 in a primary regeneration zone 36. The first separator zone 30 is in fluid communication with the primary regeneration zone 36, such as using a first conduit 38 to carry the cracking catalyst 16 from the first separation zone 30 to the primary regenerator zone 36. Air is typically used as the oxygen source 35. As the coke burns, heat and hot combustion gases are generated. Heat generation is regulated by controlling the amount of oxygen, fuel or both provided to the primary regeneration zone 36. When a substantial portion of the coke has been burned from the cracking catalyst 16 surface, the cracking catalyst 16 is separated from the combustion gases and exits the primary regeneration zone 36. The combustion gases are removed as flue gas 40. In some embodiments where there are large coke deposits, the cracking catalyst 16 is cooled in a catalyst cooler (not shown). The regeneration zone 36 is in fluid communication with the cracking zone 14, such as via a second conduit 41.

Product 28 effluent from the primary cracking zone 14 is typically processed through a product recovery section 42. Methane, ethane, ethylene, propane, propylene, light naphtha, heavy naphtha, cycle oil and gas oil are all potential products recovered from the primary cracking zone product 28. The exact products 28 derived from the catalytic cracking process depend on the catalytic cracking feedstock 20 selected, the exact process conditions, the cracking catalyst 16 selected, the downstream processes that are available and the current, relative economic value of the products. Light naphtha 12 from the product recovery section 42 is provided as feedstock to an olefin producing zone 50, for example, $C_4$ to $C_{10}$ naphtha, preferably $C_4$ to $C_7$ light naphtha with an olefin content of at least about 5 wt % and preferably at least about 10 to about 30 wt %.

In at least one embodiment, the olefin-producing zone 50 is a fluidized zone, or a fluidized zone optimized to produce light olefins. The olefin catalyst 52 is a small particle catalyst. The light naphtha feedstock 12 is contacted with the olefin catalyst 52 in an olefin-producing zone 50. In a second riser reactor 54, the olefin catalyst 52 cracks the feedstock and produces olefinic product as it moves up the riser 54. At the end of the second riser 54, an olefin-rich product stream 56, which is now rich in ethylene and propylene, and the olefin catalyst 52 entrained in the hydrocarbon gases enter a second separation zone 60 and are separated. The olefin-rich product hydrocarbons 56 are drawn from the top of the second separation zone 60 while the olefin catalyst 52 falls away by gravity. As in the first separation zone 30, cyclones 62 are optionally present in the second separation zone 60 to enhance separation of the olefin catalyst 52 from the olefin-rich product 56. The second separation zone 60 is in fluid communication with a regenerator 64 for the olefin catalyst 52. One example of this fluid communication is a third conduit 66 from the second separator zone 60 to the regenerator 64 for the olefin catalyst 52. Any equipment that can effect such a separation may be used, including, but not limited to, cyclone separators 62 as described above. Following separation of the olefin catalyst 52, the olefin-rich product 56 exits the second separation zone 60.

The cracking catalyst 16 has a selectivity for cracking and a selectivity for olefin production. Similarly, the olefin catalyst 52 has a selectivity for cracking and a selectivity for olefin production. In a preferred embodiment, the selectivity for cracking of the cracking catalyst 16 is greater than that of the olefin catalyst 52, while the selectivity for olefin production of the olefin catalyst 52 is greater than that of the cracking catalyst 16. In other words, the cracking catalyst 16 is more selective for cracking than the olefin catalyst 52, and the olefin catalyst 52 is more selective for olefin production than the cracking catalyst 16.

The light naphtha feedstock 12 is sent to the olefin-producing zone 54 where it reacts in the presence of an olefin catalyst 52. Any known olefin catalyst 52 can be used. For the purposes of this document, light olefins are defined as $C_3$-olefins, including ethylene and propylene. The olefin catalyst is optionally a catalyst containing zeolites with medium to strong Bronsted acidity as exemplified by ZSM-5, ZSM-11, ZSM-12, ZSM-23, ZSM-35, ZSM-38, ZSM-48, and other similar materials. U.S. Pat. No. 3,702,886, herein incorporated by reference, describes ZSM-5 in greater detail. Other suitable zeolites include ferrierite, erionite, and ST-5, developed by Petroleos de Venezuela, S. A. Preferably, the zeolite is dispersed on a matrix comprising a binder material such as silica or alumina and an inert filler material such as kaolin. These catalyst compositions have a crystalline zeolite content of 10 to 25 wt-% or more and a matrix material content of 75 to 90 wt-%. Catalysts containing about 25 wt-% crystalline zeolite materials are preferred. Greater crystalline zeolite content may be used in this catalyst, provided they have satisfactory attrition resistance. Zeolites with medium or smaller pores and low Si/Al ratio are preferred since they typically provide strong Bronsted acidity. The cracking zone catalyst may also comprise another active material such as Beta zeolite.

Any useful process conditions can be utilized in the olefin-producing zone. Temperatures range from 530° C. (986° F.) to about 650° C. (1202° F.). Pressures vary between 14.7 psi (101.3 KPa) and 64.7 psi (446 KPa). The catalyst to oil ratio is from about 1 to about 30, preferably about 1 to about 20. Variations in these conditions are due to differences in feedstock, catalyst and process equipment. In preferred embodiments, the olefin producing zone 54 is approximately 5 psi lower in pressure than the pressure in the catalytic cracking zone 14. Residence time for the light naphtha feed 12 in contact with the olefin catalyst 52 in the riser 50 is from about 0.1 to 5 seconds. The exact residence time depends upon the light naphtha feedstock 12 quality, the specific olefin catalyst 52 and the desired product 56 distribution. Short residence time assures that the desired products, such as light olefins, do not convert to undesirable products. Hence, the diameter and height of the riser 50 may be varied to obtain the desired residence time.

Coke builds up on the olefin catalyst 52, as well as on the cracking catalyst 16, and must be burned off in a second regeneration zone 64 similar to that of the first regeneration zone 36. Process conditions are selected from the same ranges as the first regeneration zone 36. However, coke accumulates on the olefin catalyst 52 to a lesser extent than the cracking catalyst 16. Use of light naphtha feedstocks 16 that are lighter in weight than catalytic cracker feedstocks 20 cause deposition of less coke on the catalyst. Because there is less coke to burn, lower temperatures are generated in the second regeneration zone 64 and heat the olefin catalyst 52 to a lower temperature. It is for this reason that temperatures in the olefin-producing zone 54 may not be able to sustain the olefin cracking reaction, or, if sustainable, may produce unacceptable yields of light olefins. Endothermic reactions in the olefin-producing zone 54 cause further reduction in the temperature of the olefin catalyst 52. The olefin producing catalyst 52 is regenerated in an environment including oxygen from an oxygen source 35 to produce the flue gas 70. Although the oxygen source 35 is shown as being from a common source, such as a main air compressor, it is to be understood that the source of oxygen is not important to this invention and that oxygen to the regenerator 64 for the olefin catalyst 52 optionally comes from a different source (not shown). The regenerator 64 for the olefin catalyst 52 is in fluid communication with the olefin producing zone 54 for transfer of the olefin catalyst 52, as by a fourth conduit 72.

To increase the temperature of the olefin catalyst 52 and to ensure that the reaction temperature is sufficient in the olefin producing zone 54, a catalyst heater 80 is installed on the path traveled by the olefin catalyst 52 between the second separator zone 60 and the entrance to the olefin producing zone 54. The catalyst heater 80 is in fluid communication with a source of hot combustion gases, individually described below. At least four embodiments of the invention described below demonstrate use of the heater 80. Referring to FIG. 1, heat is supplied to the olefin producing zone 54 by taking a portion 82 of the olefin catalyst 52 from the second separator 60 and passing it through the catalyst heater 80. The catalyst heater 80 is in fluid communication with the second separator zone 60 to receive catalyst and with the olefin producing zone 54 to discharge the catalyst. The catalyst heater 80 indirectly heats the olefin catalyst 52 and is exemplified by a heat exchanger. One example of a suitable heat exchanger 80 is a shell and tube exchanger where the olefin catalyst 52 occupies the shell side. Hot combustion gases flow through the tube side of the exchanger providing heat to the olefin catalyst 52 which returns to the olefin-producing zone 54 via conduit 84.

There are several sources for hot combustion gases in a refinery. In some cases, the source for the hot combustion gas is the primary regeneration zone 36. Catalytic cracking of the heavier feedstocks 20, particularly resids, deposit large amounts of coke, which, when burned, generates large amounts of heat. The flue gas from the primary regeneration zone 36 is directed to the tube side of the heater 80. After heating in the shell side of the catalyst heater 80, the olefin catalyst 52 is returned to the entrance to the olefin producing zone 54. In this embodiment, the portion of the olefin catalyst 52 that is heated bypasses the regenerator 64 for the olefin catalyst 52 and is reintroduced into the olefin producing zone 54 without burning coke from the surface. Where coke build up is low, more heat is obtained by heating than by regeneration of this portion of the olefin catalyst 52.

Figure 2:
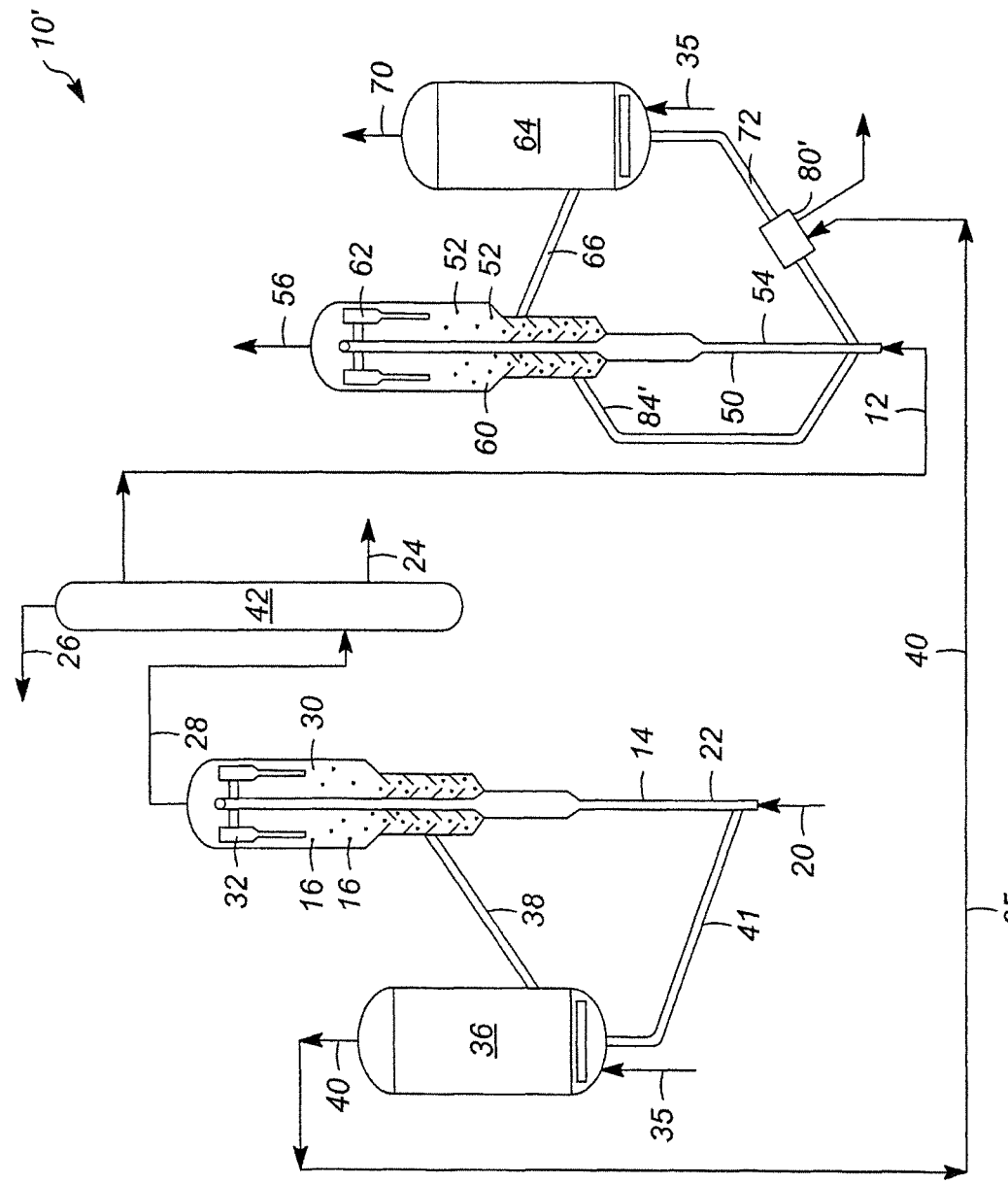
FIG. 2 is a schematic drawing of a second embodiment of the invention.

Referring to FIG. 2, a second embodiment generally 10' is shown whereby the olefin catalyst 52 is heated along the path it travels between the exit of the regenerator 64 for the olefin catalyst 52 and the entrance to the olefin producing zone 54. The heater 80' is positioned to accept at least a portion of the olefin catalyst 52 from the regeneration zone 64 for the olefin catalyst 52. Hot combustion gases 40 from the primary regeneration zone 36 provide heat that is transferred in duct 85 to the olefin catalyst 52. If less than all of the olefin catalyst 52 is heated, the heated portion is recombined with the unheated portion. The olefin catalyst 52 is then sent to the entrance to the olefin producing zone 54.

Optionally, a portion of the olefin catalyst 52 can be recycled through conduit 84' to the entrance of the olefin producing zone 54 without heating.

Figure 3:
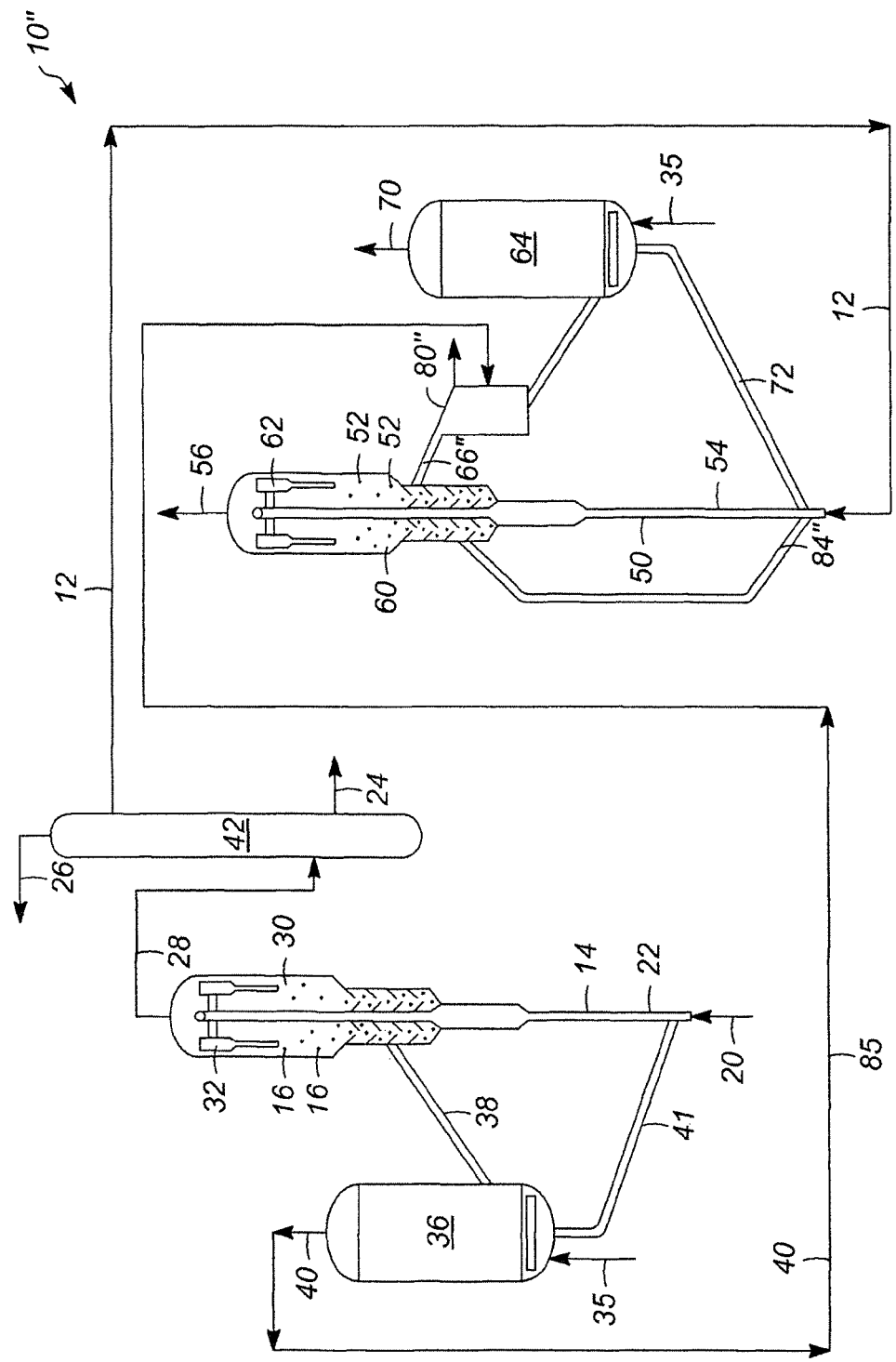
FIG. 3 is a schematic drawing of a third embodiment of the invention.

Referring to FIG. 3, a third embodiment generally 10" is shown whereby at least a portion the olefin catalyst 52 is heated along the path it travels between the second separator zone 60 and the entrance to the regenerator 64. The heater 80" is positioned to accept at least a portion of the olefin catalyst 52 from the second separator zone 60. Hot combustion gases 40 from the primary regeneration zone 36 provide heat that is transferred in duct 85 to the olefin catalyst 52. The olefin catalyst 52 is then sent to the entrance to the olefin producing zone 54 through conduit 72. Optionally, a portion of the olefin catalyst 52 can be recycled through conduit 84" to the entrance of the olefin producing zone 54 without heating.

In other embodiments of the invention, the hot combustion gas to the heater 80 from the primary regeneration zone 36 is replaced or supplemented with fuel gas 86, then burned to generate additional combustion gases and heat. As the combustion gases typically have residual oxygen, it is not always necessary to supply additional oxygen, however, adding a secondary oxygen source, such as air, is an option. The fourth embodiment, below, generally 10''' is one example of adding a fuel source 86 to any of the heaters 80, 80', 80" of this invention.

Figure 4:
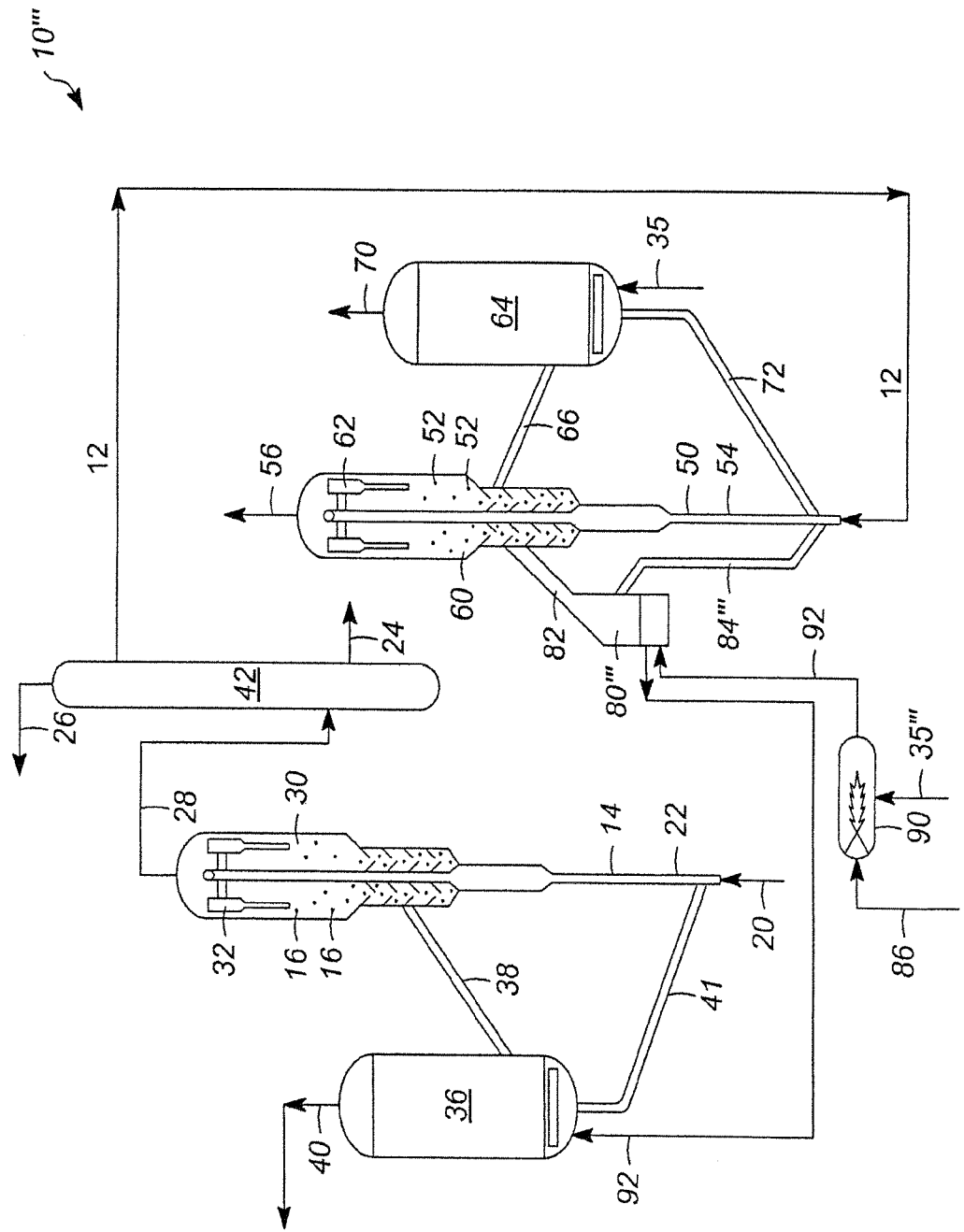
FIG. 4 is a schematic drawing of a fourth embodiment of the invention.

Turning to FIG. 4, an auxiliary fuel 86 and oxygen from the oxygen source 35''' are burned in an auxiliary heater 90, such as a direct fire air burner. The hot combustion gases 92 from the auxiliary heater 90 are passed to the olefin catalyst heater 80''' where a portion of the heat is transferred to the olefin catalyst 52. The olefin catalyst returns to the entrance of the olefin producing zone 54 through conduit 84'''. After passing through the olefin catalyst heater 80''', the hot combustion gases are sent to the primary cracking regenerator 36. There the hot gases heat the cracking catalyst 16 and initiate combustion to burn off the coke. Alternatively, the hot combustion gases 92 could be sent to the regenerator 64, or they could be split between the primary cracking regenerator 36 and the regenerator 64.

The auxiliary fuel 86 is selected from any number of gaseous streams from a refinery or associated petrochemicals plant. Examples of auxiliary fuels include methane, ethane, propane, mixtures of methane and hydrogen, mixtures of $C_4$-hydrocarbons, mixtures of hydrogen, methane and ethane, and the like.

The auxiliary heater can be used with any of the embodiments discussed, as would be understood by those of skill in the art.

Figure 5:
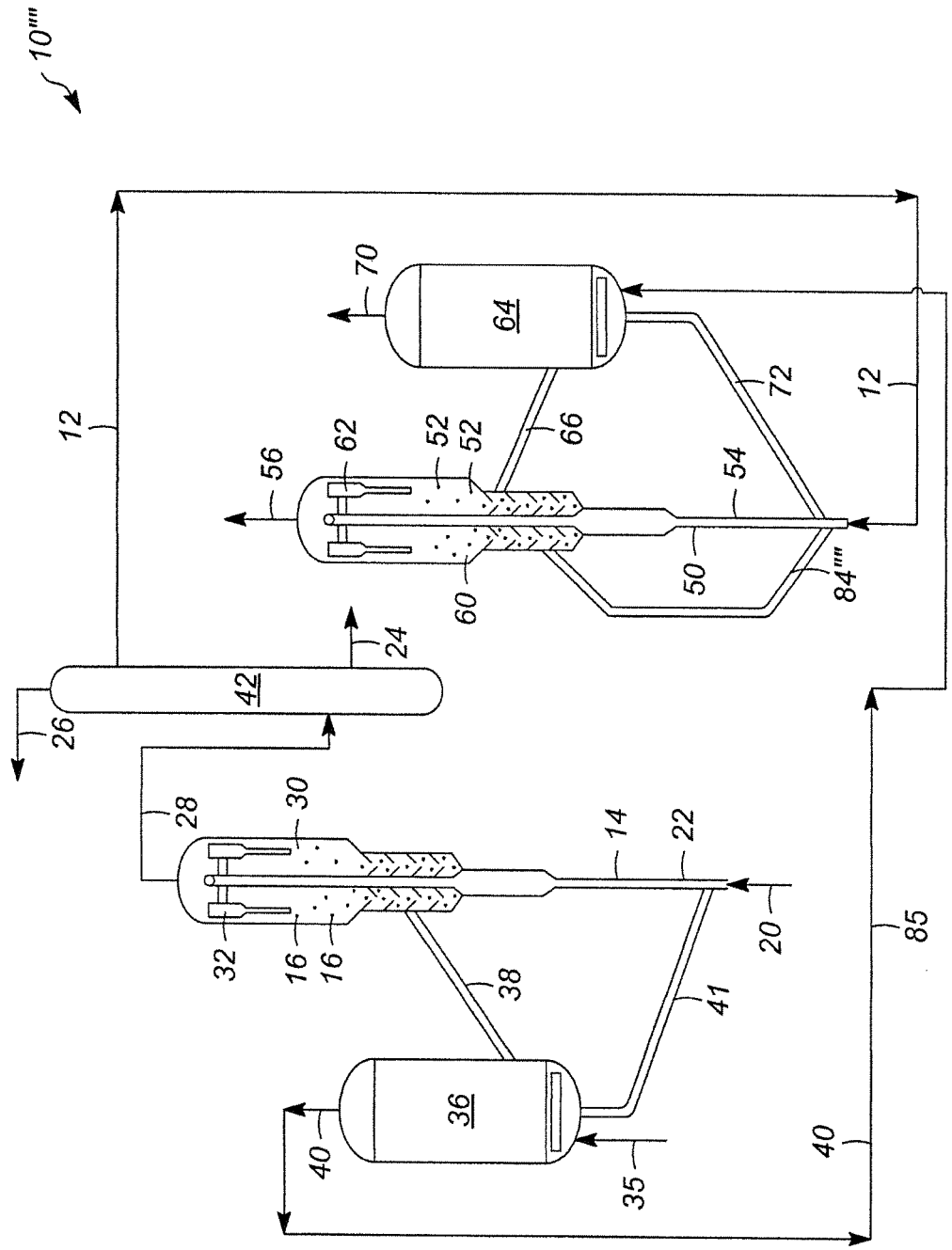
FIG. 5 is a schematic drawing of a fifth embodiment of the invention.

In another embodiment, the catalyst is directly heated by the hot combustion gases from the primary regeneration zone, rather than being indirectly heated in the heater. As shown in FIG. 5, the hot combustion gases 40 from the primary regeneration zone 36 are transferred to the regenerator 64 through duct 85. The primary process can be FCC, RFCC, or PetroFCC. The primary regeneration zone can be operated as a partial burn or a total burn, as desired. If a partial burn is used, the secondary regeneration zone converts CO to $CO_2$ and recovers heat from the flue gas. In some embodiments, sufficient heat can be generated in the olefin catalyst regenerator using only a portion of the flue gas from the cracking catalyst regenerator when it is operated either at partial or total burn. In this case, the remaining heat can be recovered for use elsewhere in the process.

The heat from the secondary regeneration zone flue gas can optionally be recovered as preheat for the feed into the olefin producing zone. The feed for the olefin producing zone can be all vapor, all liquid, or a combination of vapor and liquid.

Optionally, as previously described, a portion of the olefin catalyst 52 can be recycled through conduit 84'''' to the entrance of the olefin producing zone 54 without heating.

It is to be understood that the features of any of the embodiments discussed above may be recombined with any other of the embodiments or features disclosed herein. With respect to the embodiments depicted in the drawings, like elements have been given like numerals. Features changed from one embodiment to the next are represented by ', '', ''', and '''' respectively.

While particular features and embodiments of a process and reactor system for increasing ethylene and propylene yields has been shown and described, other variations of the invention will be obvious to those of ordinary skill in the art. All embodiments considered to be part of this invention are defined by the claims that follow.

What is claimed is:

1. A process for improving the yield of ethylene and propylene from a light naphtha feedstock, comprising:
   obtaining light naphtha feedstock from a primary cracking zone comprising a cracking catalyst;
   contacting the light naphtha feedstock with an olefin catalyst in an olefin producing zone to produce an ethylene- and propylene-rich stream;
   separating the olefin catalyst from the ethylene- and propylene-rich stream in a separator zone;
   regenerating at least a portion of the olefin catalyst by combusting coke deposited on a surface of the olefin catalyst in an oxygen-containing environment;
   directly heating at least a portion of the olefin catalyst by direct heat exchange outside of a reactor of the olefin producing zone with a stream of hot combustion gas, wherein at least a portion of the hot combustion gas is flue gas from a catalyst regenerator for the cracking catalyst; and
   returning the olefin catalyst to the olefin producing zone.

2. The process of claim 1 wherein the primary cracking zone is a fluidized bed catalytic cracking zone, a resid fluidized bed catalytic cracking zone or a fluidized bed catalytic cracking zone optimized to produce olefins.

3. The process of claim 1 wherein at least a portion of the hot combustion gas is from an auxiliary heater burning an auxiliary fuel, or oxygen or both.

4. The process of claim 3 wherein at least a portion of the hot combustion gas is supplied to the catalyst regenerator for the cracking catalyst, or the catalyst regenerator for the olefin catalyst, or both after the heating step.

5. The process of claim 1 wherein the heating step further comprises utilizing a heat exchanger to transfer heat from the hot combustion gases to the olefin catalyst.

6. The process of claim 1 further comprising separating $C_4+$ naphtha from the ethylene- and propylene-rich stream and recycling the $C_4+$ olefins to the olefin-producing zone.

7. The process of claim 1 wherein the cracking catalyst comprises zeolite Y and the olefin catalyst comprises ZSM-5.

8. The process of claim 1 wherein at least a portion of the olefin catalyst is returned to the olefin producing zone without heating or regenerating.

9. A process for improving the yield of ethylene and propylene from a light naphtha feedstock, comprising:
   obtaining light naphtha feedstock from a primary cracking zone comprising a cracking catalyst;
   contacting the light naphtha feedstock with an olefin catalyst in an olefin producing zone to produce an ethylene- and propylene-rich stream;
   separating the olefin catalyst from the ethylene- and propylene-rich stream in a separator zone;
   regenerating at least a portion of the olefin catalyst by combusting coke deposited on a surface of the olefin catalyst in an oxygen-containing environment;
   directly heating at least a portion of the olefin catalyst by direct heat exchange with a stream of hot combustion gas, wherein at least a portion of the hot combustion gas is flue gas from a catalyst regenerator for the cracking catalyst; and
   returning the olefin catalyst to the olefin producing zone.

10. The process of claim 9 wherein the olefin catalyst is directly heated with the hot combustion gas simultaneously with regenerating the olefin catalyst.

11. The process of claim 9 wherein at least a portion of the hot combustion gas is from an auxiliary heater burning an auxiliary fuel, or oxygen or both.

12. The process of claim 9 further comprising combusting CO to provide additional heat while directly heating at least the portion of the olefin catalyst with the stream of hot combustion gas.

13. The process of claim 9 wherein the stream of hot combustion gases comprises at least a portion of flue gas from a catalyst regenerator for the cracking catalyst.

14. The process of claim 9 wherein at least a portion of the olefin catalyst is returned to the olefin producing zone without heating or regenerating.

15. The process of claim 9 further comprising heating the light naphtha feedstock with hot flue gas from the catalyst regenerator for the olefin catalyst.

16. A process for improving the yield of ethylene and propylene from a light naphtha feedstock, comprising:
   obtaining light naphtha feedstock from a primary cracking zone comprising a cracking catalyst;
   contacting the light naphtha feedstock with an olefin catalyst in an olefin producing zone to produce an ethylene- and propylene-rich stream;
   separating the olefin catalyst from the ethylene- and propylene-rich stream in a separator zone;

regenerating at least a portion of the olefin catalyst by combusting coke deposited on a surface of the olefin catalyst in an oxygen-containing environment;

directly heating at least a portion of the olefin catalyst from the separator zone enroute to the entrance of a reactor of the olefin producing zone by direct heat exchange with a stream of hot combustion gas, wherein at least a portion of the hot combustion gas is flue gas from a catalyst regenerator for the cracking catalyst; and returning the olefin catalyst to the olefin producing zone.

* * * * *